US012672932B2

(12) United States Patent
Abukhalil et al.

(10) Patent No.: US 12,672,932 B2
(45) Date of Patent: Jul. 7, 2026

(54) ANATOMICAL MEASUREMENT IN A SURGICAL SYSTEM

(71) Applicant: Verb Surgical Inc., Santa Clara, CA (US)

(72) Inventors: Rami Azmi Nimer Abukhalil, West Chester, OH (US); Kenneth Fernandez Prada, Santa Clara, CA (US); Amer G. Ghanem, West Chester, OH (US); Mary Lynn Dwyer-Gaddis, Newport Beach, CA (US)

(73) Assignee: Auris Health, Inc., Santa Clara, CA (US)

( * ) Notice: Subject to any disclaimer, the term of this patent is extended or adjusted under 35 U.S.C. 154(b) by 505 days.

(21) Appl. No.: 17/986,383

(22) Filed: Nov. 14, 2022

(65) Prior Publication Data

US 2024/0156563 A1 May 16, 2024

(51) Int. Cl.
*A61B 90/00* (2016.01)
*A61B 5/00* (2006.01)
(Continued)

(52) U.S. Cl.
CPC .............. *A61B 90/06* (2016.02); *A61B 34/20* (2016.02); *A61B 34/37* (2016.02); *A61B 90/361* (2016.02);
(Continued)

(58) Field of Classification Search
CPC .................. A61B 34/20; A61B 5/6873; A61B 2017/00296; A61B 2090/061; G06N 20/00
See application file for complete search history.

(56) References Cited

U.S. PATENT DOCUMENTS 8,473,031 B2 * 6/2013 Nixon .................... A61B 34/30
600/424
9,492,240 B2 11/2016 Itkowitz et al.
(Continued)

FOREIGN PATENT DOCUMENTS

WO WO-2006033721 A1 * 3/2006 ......... A61B 1/00071
WO WO-2008144766 A1 * 11/2008 ........... A61B 5/0059
(Continued)

OTHER PUBLICATIONS

Method for Horizontal Calibration of Laser-Projection Transnasal Fiberoptic High-Speed Videoendoscopy, Hamzeh et al. HHS Public Access, Appl Sci (Basel). Author manuscript; available in PMC Jan. 2, 2022, Appl Sci (Basel). Jan. 2021 (Year: 2022).*
(Continued)

*Primary Examiner* — Sean P Dougherty
(74) *Attorney, Agent, or Firm* — Lempia Summerfield Katz LLC

(57) ABSTRACT

For anatomy measurement in a surgical system, a machine-learned model is used to determine the location or length. For example, in RYGB, the machine-learned model indicates how much of the bowel has been pulled or run. As another RYGB example, the machine-learned model indicates a length along the bowel to a current location. In yet another RYGB example, the machine-learned model indicates a location for incision based on a desired length. Using an image or images, such as a video stream from an endoscope, the artificial intelligence provides the measurement, avoiding running with estimated steps size or use an inserted ruler.

15 Claims, 6 Drawing Sheets

(51) Int. Cl.

| | | |
|---|---|---|
| *A61B 17/00* | (2006.01) | |
| *A61B 34/20* | (2016.01) | |
| *A61B 34/30* | (2016.01) | |
| *A61B 34/37* | (2016.01) | |
| *G06T 7/00* | (2017.01) | |

(52) U.S. Cl.
CPC .......... *G06T 7/0012* (2013.01); *A61B 5/6873*
(2013.01); *A61B 2017/00296* (2013.01); *A61B*
*2034/2065* (2016.02); *A61B 2034/301*
(2016.02); *A61B 2034/305* (2016.02); *A61B*
*2090/061* (2016.02); *G06T 2207/20081*
(2013.01)

(56) References Cited

U.S. PATENT DOCUMENTS

| | | | | |
|---|---|---|---|---|
| 9,545,220 | B2 * | 1/2017 | Sidlesky | ............... A61B 5/7475 |
| 10,299,698 | B2 * | 5/2019 | Duindam | ............... A61B 5/066 |
| 12,186,135 | B2 * | 1/2025 | Mai | ......................... A61B 34/25 |
| 2002/0118867 | A1 * | 8/2002 | Barfuss | ................ G06V 10/752 |
| | | | | 382/128 |
| 2008/0249356 | A1 * | 10/2008 | Motai | ................ A61B 1/00082 |
| | | | | 600/114 |
| 2009/0171371 | A1 * | 7/2009 | Nixon | .................... A61B 34/37 |
| | | | | 700/264 |
| 2009/0190808 | A1 * | 7/2009 | Claus | ................... A61B 3/0041 |
| | | | | 382/128 |
| 2010/0317965 | A1 * | 12/2010 | Itkowitz | ................ A61B 34/30 |
| | | | | 382/128 |
| 2012/0143172 | A1 * | 6/2012 | Oko | ................ A61B 17/00234 |
| | | | | 606/1 |
| 2013/0303890 | A1 * | 11/2013 | Duindam | ............... A61B 5/065 |
| | | | | 382/103 |
| 2019/0362834 | A1 * | 11/2019 | Venkataraman | ....... G06V 20/41 |
| 2020/0015926 | A1 * | 1/2020 | Mata | .................... A61B 90/361 |
| 2020/0069264 | A1 * | 3/2020 | Merritt | .................... A61B 6/486 |
| 2020/0214777 | A1 * | 7/2020 | Itkowitz | ................ B25J 9/1682 |
| 2021/0256719 | A1 * | 8/2021 | Hufford | .................... G06T 7/70 |
| 2022/0087768 | A1 | 3/2022 | Mai et al. | |
| 2022/0383607 | A1 * | 12/2022 | Usuda | .................... G16H 30/40 |

FOREIGN PATENT DOCUMENTS

| | | | | |
|---|---|---|---|---|
| WO | WO-2010129911 A1 * | 11/2010 | .......... | G06T 7/0012 |
| WO | WO-2021097461 A1 * | 5/2021 | ............. | A61B 34/25 |

OTHER PUBLICATIONS

Bodenstedt, Sebastian, et al. "Image-based laparoscopic bowel measurement." International journal of computer assisted radiology and surgery 11.3 (published online Sep. 26, 2015): 1-14.

* cited by examiner

ANATOMICAL MEASUREMENT IN A SURGICAL SYSTEM

FIELD

Embodiments relate to anatomical (e.g., biliary and/or alimentary loop) measurement in a surgical system.

BACKGROUND

Minimally invasive surgery (MIS) reduces tissue damage during a surgical procedure, Robotic systems may perform MIS. The robotic systems include one or more robotic arms for manipulating surgical tools based on commands from a remote operator. Other surgical systems, such as using scopes and catheters directly or manually controlled by the surgeon, may be used to perform MIS.

During MIS, surgeons may need to measure lengths of tissues or organs in preparation to transect, suture, or otherwise incise the tissues or organs. For example, during a Roux-en-Y gastric bypass (RYGB) or a mini gastric bypass procedure, a surgeon performs two length measurements of the patient's intestines. The biliary loop and alimentary loop are both measured to form the limbs of RYGB. In another example, a surgeon often determines the exposed vaginal length during a vaginal dissection procedure. As another example, during a RYGB reconstruction phase of a total gastrectomy procedure, the jejunum is directly connected to the esophagus. To choose the starting position of the jejunum, a length of jejunum is typically measured 30-40 cm downstream from the ligament of Treitz. In addition, the surgeon measures another 60-70 cm of jejunum to determine the location to start the jejunojejunostomy. The surgeon ensures that the selected section of jejunum is sufficiently long to reach the esophagus.

Traditional tissue or organ length measurements are performed using a physical ruler inserted into patient's body and placed in the vicinity of the surgical site. For example, in MIS, a disposable paper ruler is delivered into a patient's body through an accessory port. The ruler is held in front of the target anatomy for the length measurements. After noting the measurements, the surgeon then passes the ruler back for removal. However, using a physical ruler for surgical length measurements is intrinsically cumbersome, increases total operation time, and does not apply to certain length measurement situations.

Another common length measurement is based on visual estimations. To measure these desired lengths of the bowel, the surgeon visually estimates a distance by counting a number of grasps on the bowel with two surgical instruments using a hand-over-hand technique referred to as "running the bowel." By grasping the bowel with 5 cm between the two instruments each time, the surgeon counts the number of grasps and subsequently determines the total length of the bowel traveled or pulled. Unfortunately, this visual estimation technique is highly susceptible to the experience level of the surgeon and is inherently inaccurate.

SUMMARY

By way of introduction, the preferred embodiments described below include methods, systems, instructions, and computer readable media for anatomy measurement in a surgical system. A machine-learned model is used to determine the location or length. For example, in RYGB, the machine-learned model indicates how much of the bowel has been pulled or run. As another RYGB example, the machine-learned model indicates a length along the bowel to a current location. In yet another RYGB example, the machine-learned model indicates a location for incision based on a desired length. Using an image or images, such as a video stream from an endoscope, the artificial intelligence provides the measurement, avoiding running with estimated steps size or use an inserted ruler.

In a first aspect, a method is provided for loop measurement for a surgical system. An endoscope captures a video stream intra-operatively during minimally invasive surgery. A machine-learned model measures a length along a biliary loop or an alimentary loop in response to input of the video stream. The length or a location based on the length is displayed during the minimally invasive surgery.

In one embodiment, the video stream is captured with the endoscope held by a robotic arm. For example, a surgical robotic system moves the endoscope while capturing the video. In another embodiment, the endoscope is moved manually by a physician while capturing the video.

Various outputs may be provided by the machine-learned model. For example, the machine-learned model outputs the length along the biliary loop or alimentary loop at which a surgical instrument is located. As another example, the machine-learned model outputs the length as a position along the biliary loop or alimentary loop for operating on the biliary loop or alimentary loop. In yet another example, the machine-learned model outputs a length traversed along the biliary or alimentary loop.

In an embodiment, the length is displayed as a measurement of a current distance along the biliary loop or the alimentary loop. According to another embodiment, the location for operating on tissue is displayed. The location is determined from the length along the biliary loop or the alimentary loop.

In a second aspect, a surgical system is provided for measurement during surgery. A medical imager is configured to capture an image of anatomy during surgery for the anatomy. An image processor is configured to determine, by a machine-learned model in response to input of the image, a distance along the anatomy. A display is configured to display a location of the anatomy during the surgery based on the distance determined by the machine-learned model.

According to one embodiment, the medical imager is an endoscope. A first robotic arm is configured to move the endoscope within a patient where the image is from within the patient. As a further embodiment, a second robotic arm is configured to pull (run) the anatomy with the endoscope positioned outside the anatomy. The distance is an amount of the anatomy pulled by the second robotic arm.

In another embodiment, the surgery is gastric bypass surgery, and the distance is a distance along a biliary or alimentary loop.

As one embodiment, the location is a current location of a surgical tool with the distance to the surgical tool along the anatomy.

As yet another embodiment, the location is the location for surgery on the anatomy, such as a location for incision.

The location may be displayed in various manners. For example, the display is configured to display the location on the image. As another example, the display is configured to display the location on a pre-operative image.

In a third aspect, a method is provided for machine training a model for measuring during surgery. Training data of surgical images and lengths along anatomy in the surgical images is obtained. The model is machine trained with the training data. The model is machine trained to output the lengths in response to input of the surgical images. The machine-trained model is stored.

In one embodiment, the surgical images are video streams from endoscopes in gastric bypass surgeries. The lengths are lengths of biliary or alimentary loops being pulled for measurement. The machine training is training the model to output the length being pulled for measurement.

In another embodiment, the lengths for the training data are measured with an optical sensor and laser projector.

In yet another embodiment, the training data is obtained for a surgical robotic system. The machine training is for the model for the surgical robotic system.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The embodiments of the invention are illustrated by way of example and not by way of limitation in the figures of the accompanying drawings in which like references indicate similar elements. It should be noted that references to "an" or "one" embodiment of the invention in this disclosure are not necessarily to the same embodiment, and they mean at least one. Also, in the interest of conciseness and reducing the total number of figures, a given figure may be used to illustrate the features of more than one embodiment of the invention, and not all elements in the figure may be required for a given embodiment.

DETAILED DESCRIPTION

During surgery, anatomy is measured to locate a position for incision or other operation on the anatomy. For example, biliary and/or alimentary loops are measured to find the locations for gastric bypass. Rather than visual estimation, measuring with a tape measure inserted into the patient, or estimation by running, artificial intelligence determines the length or location on the anatomy based on input images. For example, a video stream from an endoscope within the patient provides a sequence of images. The artificial intelligence, in response to input of the images, outputs a measurement. The machine-learned model may instead be trained and used to estimate length or incision location pre-operatively.

The measurement is performed during minimally invasive surgery. The example surgical procedure used herein is Roux-en-Y Gastric Bypass (RYGB). The measurement in this example occurs during RYGB. The artificial intelligence-based measurement may be used for other bypass surgeries, such as gastrectomy or gastric bypass. The artificial intelligence-based measurement may be used for any other surgical procedures, such as vaginal dissection procedure or another minimally invasive surgery. The artificial intelligence-based measurement may be used at other times, such as pre-operatively.

Figure 3:
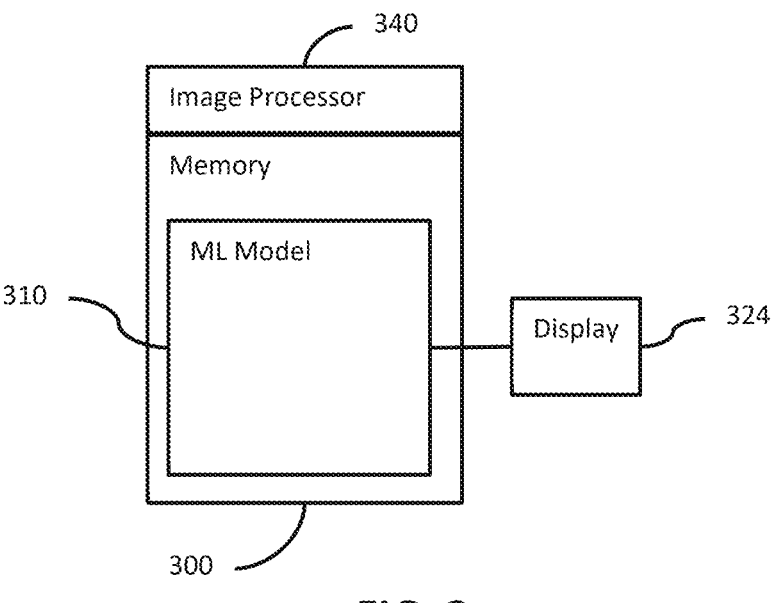
FIG. 3 is a block diagram of another embodiment of a surgical system using a machine-learned model to measure.
Figure 4:
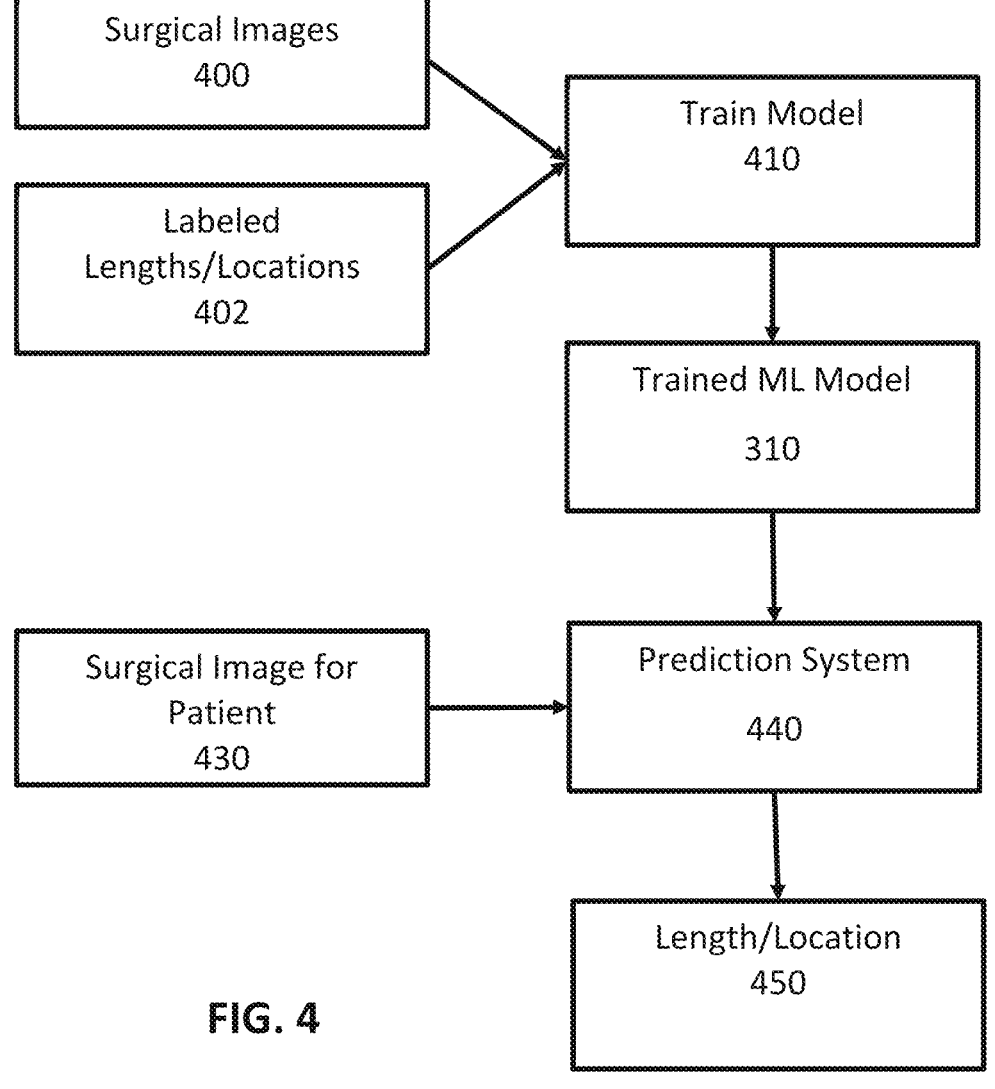
FIG. 4 is a flow chart diagram of one embodiment of a method for surgical measuring with artificial intelligence.
Figure 5:
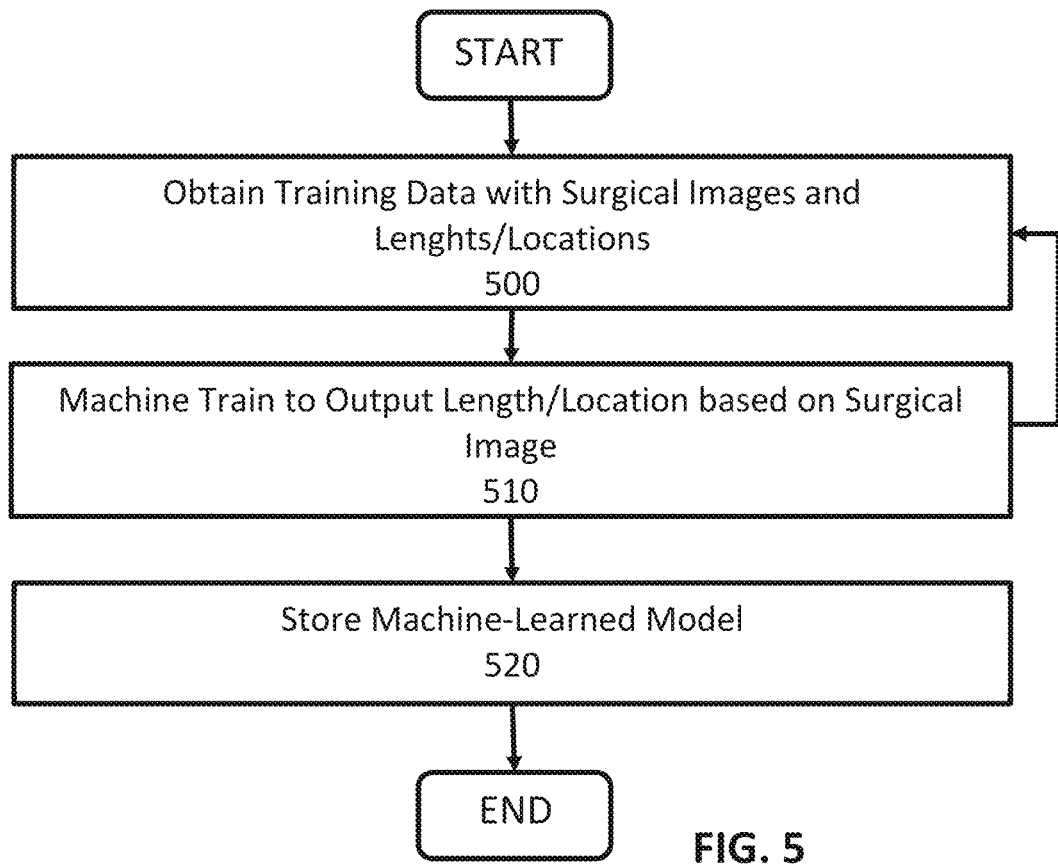
FIG. 5 is a flow chart diagram of one embodiment of a method for machine training to measure anatomical length in surgery.
Figure 6:
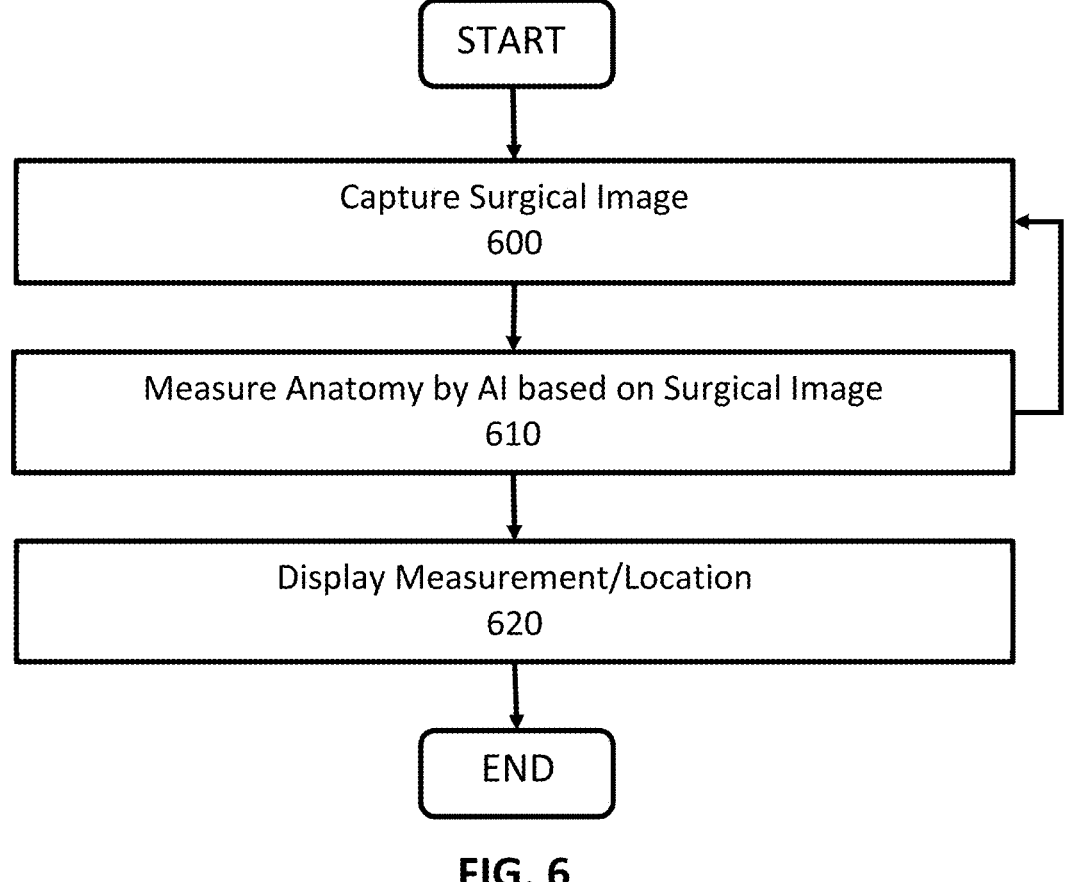
FIG. 6 is a flow chart diagram of one embodiment of a method for measuring length using artificial intelligence.

The discussion below first introduces an example surgical robotic system (see FIGS. 1 and 2). FIG. 3 is directed to a surgical system for use of a machine-learned model in surgical measurement. FIGS. 4-6 show embodiments for training the machine-learned model and/or measurement using the machine-learned model as trained.

The surgical robotic system may have any arrangement, such as one or more robotic arms. One or more surgical instruments may be used, such as graspers, clamps, endoscope, and/or scalpel instruments. FIGS. 1 and 2 show an example robotic surgery system. Other surgical instruments, robotic arms, and/or robotic surgery systems may be used. In other embodiments, the surgical system is provided for use without robotics, such as a surgical system relying on direct, manual control by a surgeon.

Figure 1:
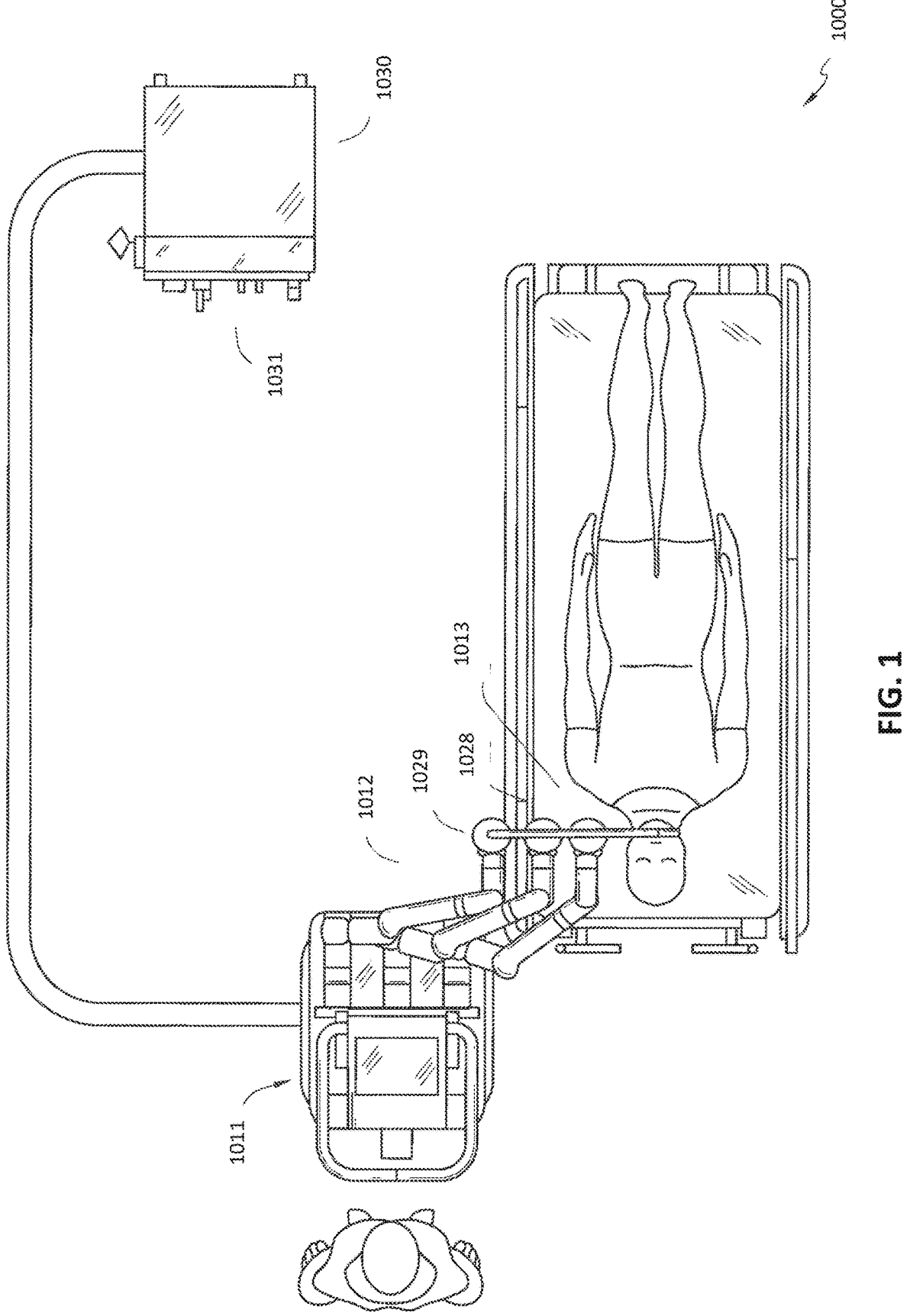
FIG. 1 illustrates an embodiment of a cart-based robotic system arranged for diagnostic and/or therapeutic use.

FIG. 1 shows an embodiment of a surgical robotic system. The robotically-enabled medical system may be configured in a variety of ways depending on the particular procedure. In FIG. 1, the surgical robotic system is a cart-based robotically-enabled system 1000 arranged for a diagnostic and/or therapeutic surgery, such as bronchoscopy. The system 1000 may include a cart 1011 having one or more robotic arms 1012 to deliver a medical instrument, such as a steerable endoscope 1013 and/or therapeutic tools. The cart 1011 may be positioned proximate to the patient's upper torso to provide access to an access point. Similarly, the robotic arms 1012 may be actuated to position the instruments. The arrangement in FIG. 1 with the arms 1012 repositioned may be utilized when performing a gastro-intestinal (GI) procedure with a gastroscope, RYGB, or a specialized endoscope for GI procedures.

Once the cart 1011 is properly positioned, the robotic arms 1012 may insert the steerable endoscope 1013 into the patient robotically, manually, or a combination thereof. The steerable endoscope 1013 may include at least two telescoping parts, such as an inner leader portion and an outer sheath portion, each portion coupled to a separate instrument driver from the set of instrument drivers 1028, each instrument driver coupled to the distal end of an individual robotic arm 1012, This linear arrangement of the instrument drivers 1028, which facilitates coaxially aligning the leader portion with the sheath portion, creates a "virtual rail" 1029 that may be repositioned in space by manipulating the one or more robotic arms 1012 into different angles and/or positions. The virtual rails described herein are not any physical structure of the system but an arrangement of other structures. Translation of the instrument drivers 1028 along the virtual rail 1029 telescopes the inner leader portion relative to the outer sheath portion or advances or retracts the endoscope 1013 from the patient. The angle of the virtual rail 1029 may be adjusted, translated, and pivoted based on clinical application or physician preference. For example, in bronchoscopy, the angle and position of the virtual rail 1029 as shown represents a compromise between providing physician access to the endoscope 1013 while minimizing friction that results from bending the endoscope 1013 into the patient's mouth. Similarly, for RYGB, the endoscope is inserted through a port in the patient, so the angle and position of the virtual rail 1029 is oriented about that access point. The virtual rail may not be used for some procedures, such as RYGB.

The endoscope 1013 may be directed within the patient after insertion using precise commands from the robotic system until reaching the target destination or operative site. To enhance navigation and/or reach the desired target, the endoscope 1013 may be manipulated to telescopically extend the inner leader portion from the outer sheath portion to obtain enhanced articulation and greater bend radius. The use of separate instrument drivers 1028 also allows the leader portion and sheath portion to be driven independently of each other.

The system 1000 may also include a movable tower 1030, which may be connected via support cables to the cart 1011 to provide support for controls, electronics, fluidics, optics, sensors, and/or power to the cart 1011. Placing such functionality in the tower 1030 allows for a smaller form factor cart 1011 that may be more easily adjusted and/or repositioned by an operating physician and his/her staff. Additionally, the division of functionality between the cart/table and the support tower 1030 reduces operating room clutter and facilitates improving clinical workflow. While the cart 11 may be positioned close to the patient, the tower 1030 may be stowed. In a remote location to stay out of the way during a procedure.

In support of the robotic systems described above, the tower 1030 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 1030 or the cart 1011, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 1030 may also include a pump, flow meter, valve control, and/or fluid access to provide controlled irrigation and aspiration capabilities to the system that may be deployed through the endoscope 1013. The tower 30 may include a voltage and surge protector designed to provide filtered and protected electrical power to the cart 11, thereby avoiding placement of a power transformer and other auxiliary power components in the cart 1011, resulting in a smaller, more moveable cart 1011. The tower 1030 may also include support equipment for the sensors deployed throughout the robotic system 1000. Similarly, the tower 1030 may also include an electronic subsystem for receiving and processing signals received from deployed electromagnetic (EM) sensors. The tower 1030 may also be used to house and position an EM field generator for detection by EM sensors in or on the medical instrument.

The tower 1030 may also include a console 1031 in addition to other consoles available in the rest of the system, e.g., console mounted on top of the cart. The console 1031 may include a user interface and a display screen, such as a touchscreen, for the physician operator. Consoles in the system 1000 are generally designed to provide both robotic controls as well as preoperative and real-time information of the procedure, such as navigational and localization information of the endoscope 13. When the console 1031 is not the only console available to the physician, it may be used by a second operator, such as a nurse, to monitor the health or vitals of the patient and the operation of the system 1000, as well as to provide procedure-specific data, such as navigational and localization information. In other embodiments, the console 1031 is housed in a body that is separate from the tower 1030.

Embodiments of the robotically-enabled medical system may also incorporate the patient's table. Incorporation of the table reduces the amount of capital equipment within the operating room by removing the cart, which allows greater access to the patient. FIG. 2 illustrates an embodiment of such a robotically-enabled system. The system 1136 includes a support structure or column 1137 for supporting platform 1138 (shown as a "table" or "bed") over the floor. Much like in the cart-based systems, the end effectors of the robotic arms 1139 of the system 1136 comprise instrument drivers that are designed to manipulate an elongated medical instrument, such as an endoscope, grasper, and/or scalpel.

The column 1137 may include one or more carriages 1143 shown as ring-shaped in the system 1136, from which the one or more robotic arms 1139 may be based. The carriages 1143 may translate along a vertical column interface that runs the length of the column 1137 to provide different vantage points from which the robotic arms 1139 may be positioned to reach the patient. The carriage(s) 1143 may rotate around the column 1137 using a mechanical motor positioned within the column 1137 to allow the robotic arms 1139 to have access to multiples sides of the table 1138, such as, for example, both sides of the patient. In embodiments with multiple carriages 1143, the carriages 1143 may be individually positioned on the column 1137 and may translate and/or rotate independently of the other carriages. While the carriages 1143 need not surround the column 1137 or even be circular, the ring-shape as shown facilitates rotation of the carriages 1143 around the column 1137 while maintaining structural balance. Rotation and translation of the carriages 1143 allows the system 1136 to align the medical instruments into different access points on the patient. In other embodiments (not shown), the system 1136 can include a patient table or bed with adjustable arm supports in the form of bars or rails extending alongside it. One or more robotic arms 1139 (e.g., via a shoulder with an elbow joint) can be attached to the adjustable arm supports, which can be vertically adjusted. By providing vertical adjustment, the robotic arms 1139 are advantageously capable of being stowed compactly beneath the patient table or bed, and subsequently raised during a procedure.

The robotic arms 1139 may be mounted on the carriages 1143 through a set of arm mounts 1145 including a series of joints that may individually rotate and/or telescopically extend to provide additional configurability to the robotic arms 1139. Additionally, the arm mounts 1145 may be positioned on the carriages 1143 such that, when the carriages 1143 are appropriately rotated, the arm mounts 1145 may be positioned on either the same side of the table 1138, on opposite sides of the table 1138, or on adjacent sides of the table 1138.

The column 1137 structurally provides support for the table 1138, and a path for vertical translation of the carriages 1143. Internally, the column 1137 may be equipped with lead screws for guiding vertical translation of the carriages, and motors to mechanize the translation of the carriages 1143 based on the lead screws. The column 1137 may also convey power and control signals to the carriages 1143 and the robotic arms 1139 mounted thereon.

Figure 2:
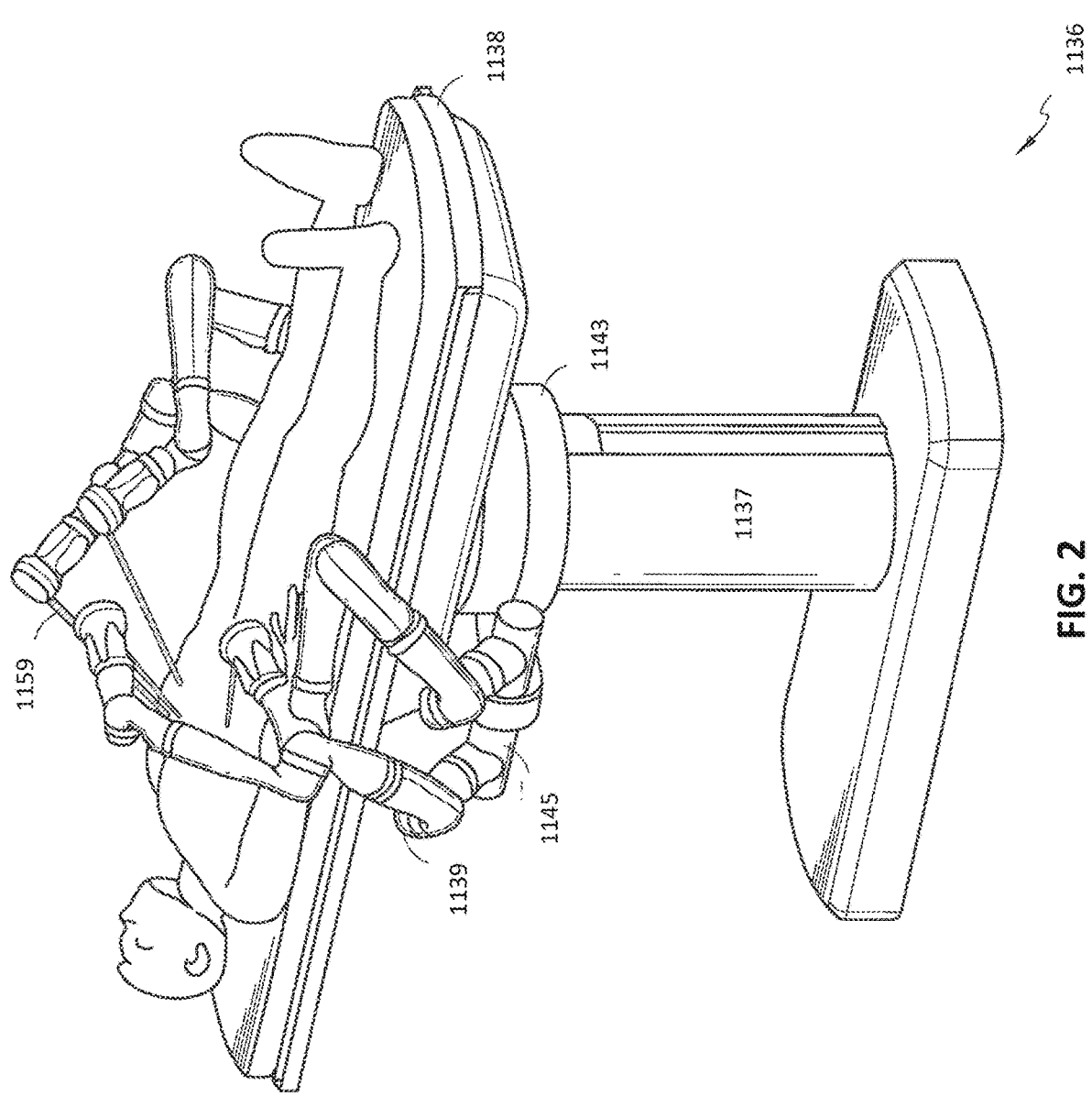
FIG. 2 illustrates an embodiment of a table-based robotic system configured for a procedure.

In one embodiment, the robotic surgical system of FIG. 2 is used for RYGB. In a laparoscopic procedure, through small incision(s) in the patient's abdominal wall, minimally invasive instruments may be inserted into the patient's anatomy. In some embodiments, the minimally invasive instruments include an elongated rigid member, such as a shaft, which is used to access anatomy within the patient. After inflation of the patient's abdominal cavity, the instruments may be directed to perform surgical or medical tasks, such as grasping, cutting, ablating, suturing, etc. in some embodiments, the instruments include a scope, such as a laparoscope or another endoscope for a viewing task, not necessarily surgical in the sense of operating directly on tissue, one or more graspers for manipulating intestine, and a scalpel for creating a bypass. Apure 2 illustrates an embodiment of a robotically-enabled, table-based system configured for a laparoscopic procedure, such as RYGB or another gastric bypass. As shown in FIG. 2, the carriages 1143 of the system 1136 may be rotated and vertically adjusted to position pairs of the robotic arms 1139 on opposite sides of the table 1138, such that instruments 1159 may be positioned using the arm mounts 1145 to be passed through minimal incisions (ports) on both sides of the patient to reach his/her abdominal cavity, RYGB may then be performed using one or more drivers with the surgical instruments or tools.

FIG. 3 shows one embodiment of a surgical system for measurement during surgery. The system is a workstation, computer, controller, server, tablet, or mobile device, in one embodiment, the system is part of the surgical robot, such as being in the tower 1030 or cart 1011. In another embodiment, the system communicates wirelessly and/or wired (e.g., over a computer network) with the robotic system 1000, 1136. In other embodiments, the system provides information to a surgeon for assisting the surgeon in manual operation of catheters, endoscopes, and/or other tools for MIS.

Via communications and/or physical connection, the system of FIG. 3 connects with one or more of the robotic arms, such as connecting with the surgical robot or system 1000, 1136. Interaction with the arms 1139 of FIG. 2 will be used in examples below, but interaction with other robotic arms (e.g., arms 1012 of FIG. 1) may be used in other examples. The robotic arm(s) 1139 are configured to hold and operate surgical tool(s) 1159.

The surgical system includes an image processor 340, a memory 300, and a display 342. Additional, different, or fewer devices may be provided. For example, an output interface, such as a network card, network adaptor, graphics card, or display buffer, is provided between the image processor 340 and/or memory 300 and a computer network and/or the display 324.

The surgical system may include a medical imager. In one embodiment, the medical imager is an endoscope 1013, such as a laparoscope. The medical imager is insertable, at least partially, within the patient to image from within the patient. For example, the scope includes a lens with fiberoptics and/or a camera insertable into the patient, in alternative embodiments, the medical imager is an ultrasound, computed tomography (CT), x-ray, magnetic resonance (MR), or another scanner for imaging the Interior of the patient from outside of the patient. Endoscope examples are used below.

The medical imager is configured by hardware, software, and/or firmware to capture one or more images of anatomy during surgery on or for the anatomy. For example, the endoscope is configured to capture an image or sequence of images (e.g., video) with a camera while the endoscope is within the patient. One of the robotic arms 1139 is configured to move the endoscope within the patient during the surgery, such as moving the endoscope to view a bowel of the patient. The movement may be along the anatomy or to view the anatomy where the surgeon then moves the anatomy relative to the camera position. Other robotic arms 1139 are configured to move (e.g., pull or run) the anatomy with the endoscope positioned outside of the anatomy. In alternative embodiments, the medical imager images the interior of the patient.

The processor 340 is a general processor, application specific integrated circuit, field programmable gate array, digital signal processor, controller, artificial intelligence processor, tensor processor, graphics processing unit, digital circuit, analog circuit, combinations thereof, and/or other now known or later developed processor for anatomy measurement using artificial intelligence. The processor 340 is configured by software, hardware, and/or firmware to apply the artificial intelligence and/or determine a position or length along anatomy.

The processor 340 is configured to determine a distance along the anatomy. In some cases, the anatomy is manipulated during the determination. Rather than detecting a distance based on a range between to points and a resolution with a single image, the distance is determined while the anatomy is pulled or minipulated. Other actions may occur as part of the determination, such as moving, clamping, pressing, pulling, running, or otherwise manipulating the tissue during surgery. The processor 340 is configured to determine the length or location a given length from a starting point while accounting for any manipulation of the anatomy. For example, the biliary and/or alimentary loops of the bowel are run where one or more graspers move or pull the bowel along to measure the distance. In alternative embodiments, the length and/or location based on length are determined without any manipulation of the anatomy being measured.

The processor 340 is configured to measure using an artificial intelligence. In one embodiment, the artificial intelligence outputs the length or distance in response to input of information. In another embodiment, the artificial intelligence outputs a location a given length from a starting location. In alternative embodiments, the artificial intelligence outputs information used to then determine the length and/or location, such as outputting a step size between graspers 1159 used to pull the bowel. The processor 340 is configured to apply the artificial intelligence and use the output to then measure.

The processor 340 may be configured to perform other processing, such as pre-processing (e.g., normalization or scaling) of the input to the artificial intelligence or post-processing of the output of the artificial intelligence.

The artificial intelligence outputs in response to an input. Any of various inputs may be used, such as one or more surgical images. For example, a video stream from an endoscope is input. The video stream may have any frequency, such as 20 Hz. Sampling may be used, such as a video stream at 1 Hz sampled from a sequence of images captured at a greater frequency. As another example, manually or view triggered images are input, such as an image at a beginning of pulling and images at occurrence of grasping, completion of instrument 1159 movement, or other triggers. In yet other examples, a single image is captured and used. Surgical images represent the patient while the surgery is occurring, such as with an endoscope within the patient or imaging from an exterior while one or more instruments 1159 are within the patient.

Other information may be included, such as clinical information for the patient (e.g., age, sex, height, weight, body mass index, blood test results, fecal examination results, and/or other information). Pre-operative images with or without labeled information (e.g., planned location for incision and/or pre-operatively measured length).

The artificial intelligence generates one or more outputs. For example, the output is the length or distance to a location, such as length having been pulled or run so far (i.e., length to a current grasp point on the bowel). As another example, the output is a location at a given length from a starting point, such as an intermediate location or the final incision location.

The artificial intelligence is a machine-learned model 310. In the example embodiment of FIG. 3, the machine-learned model 310 stored in the memory 300 is configured by training to receive the input (e.g., video stream) and generate the output.

The machine-learned model 310 was previously trained using machine learning as represented in FIG. 4. Machine learning is an offline training phase where the goal is to identify an optimal set of values of learnable parameters of the model 310 that can be applied to many different inputs (i.e., previously unseen inputs for a given patient). In this example, the training data is many samples of input surgical images 400 with labeled lengths and/or locations 402 as the ground truth. After training 410, a trained ML model 310 results. The trained ML model 310 includes the values of the machine-learned parameters of the model 310. The machine-learned parameters can subsequently be used during operation (testing or application phase) by the prediction system 440 to rapidly generate the output. Once learned, the machine-learned model 310 is used in an online processing phase in which the input for a given patient (e.g., surgical image 430) is input, and the location and/or length 450 or information used to determine the location and/or length 450 is output based on the model values learned during the training phase. The location and/or length 450 for incision and/or having been run, respectively, for the bowel undergoing surgery (intra-operative location) is output.

Returning to FIG. 3, various types of machine learning models may be used, such as support vector machines, neural networks, Bayesian, regression, or another. In one embodiment, the model is a neural network, such as a fully connected neural network or a convolutional neural network. For example, a multi-layer perceptron neural network is used. As another example, a regression model, such as linear, logistic, ridge, Lasso, polynomial, or Bayesian linear regression model is used. Any architecture or layer structure for machine learning may be used, such as a convolutional neural network. The architecture defines the structure, learnable parameters, and relationships between parameters. Different machine-learned models 310 may be used for different outputs, such as different models or a multi-task model to generate location of incision and traveled or run length.

The model 310 is machine trained. Deep or other machine training is performed. Many (e.g., hundreds or thousands) samples of inputs to the model and the ground truth outputs are collected as training data. For example, data from testing (e.g., on cadavers) or from usage (e.g., from surgeries performed on patients) is collected as training data. Simulation may be used to generate the training data. Experts may curate the training data, such as assigning ground truth for collected samples of inputs. Training data may be created from a guideline or statistical shape model. Measurement tools, such as rulers, camera, and/or optical sensors, may be used to collect the ground truth for the samples. Many samples for a given surgery may be collected.

The machine training optimizes the values of the learnable parameters. Backpropagation, RMSprop, ADAM, or another optimization is used in learning the values of the learnable parameters of the model 310. Where the training is supervised, the differences (e.g., L1, L2, or mean square error) between the estimated output and the ground truth output are minimized.

Once trained, the model 310 is applied during surgery for a new patient. The machine-learned model 310 is used to determine the length and/or location during surgery. For example, surgical images are input during surgery, and the image processor 340 uses the machine-learned model 310 to determine a length having been run. As more bowel is pulled or run (e.g., by one or more robotic arms 1139), the machine-learned model 310 is used to update the length (e.g., amount of biliary or alimentary loop pulled by the surgical robotic system). This repetitive usage occurs until the desired length and/or corresponding location for incision is reached.

The machine-learned model 310 is previously trained, and then used as trained. Fixed values of learned parameters are used for application. The learned values and network architecture determine the output from the input. During application in surgery for a patient, the same learned weights or values are used. The model and values for the learnable parameters are not changed from one patient to the next, at least over a given time (e.g., weeks, months, or years) or given number of surgeries (e.g., tens or hundreds). These fixed values and corresponding fixed model are applied sequentially and/or by different processors to inputs for different patients. The model may be updated, such as retrained, or replaced, but does not learn new values as part of application for a given patient.

The display 324 is a screen, printer, or another hardware device that displays an image. The display 324 is configured by a display plane or buffer with an image or information from the image processor 340.

The display 324 is configured to display a location of the anatomy during the surgery based on the distance determined by the machine-learned model. The length indicates a distance from a starting location to the current location along the bowel of a surgical tool. The location may be at a length from an incision location. A location for incision (i.e., location for surgery on that anatomy) may be indicated.

The display 324 shows the estimated length and/or the predicted location. The image shows the length, such as text. In other embodiments, the image is an image from the endoscope or medical imager. The length and/or location are annotations or graphics added to the image. The length and/or location may be annotations or graphics shown on a pre-operative image.

In another embodiment, the output is to a navigation system, such as a surgical robotic system. A controller of the surgical system and/or a surgical robotic system receives the length and/or location. The instruments 1159 are controlled to run the length or to the location and/or the length and/or location is displayed by the controller.

In an example RYGB surgery, a computed tomography scan of the abdomen is performed to create a three-dimensional (3D) representation of the biliary/alimentary loop. In pre-operative planning, the length of the loop is determined, such as using software, and the ideal limb length for the Roux-en-Y is determined from the pre-operative scan data. This pre-operative information may be used during surgery to assist or guide the surgeon. For example, an electromagnetic field is created under the patient during the procedure, and the endoscope 1013 and/or other instruments 1159 are fitted with a magnetic fiducial at the distal end. The live patient is registered to the pre-operative 3D representation, and then the visualization system overlays where the incisions are to be made to achieve the desired limb lengths. The position sensing is used to guide the instruments 1159 and/or endoscope 1013 to the surgical site. The instruments 1159 may also be used to run or pull the bowel the desired length to reach the location. The artificial intelligence is used to measure the length, confirming proper location for surgery during the surgery despite any deformation occurring due to the manipulation of the anatomy.

FIG. 4 illustrates a general framework for machine learning and application of the machine-learned model. FIG. 5 is a flow chart diagram of one embodiment of a method for machine training 410. FIG. 6 is a flow chart diagram of one embodiment of a method for application of the machine-learned model 310.

FIG. 5 is a flow chart diagram of one embodiment of a method for machine training for measuring during surgery. The acts are performed in the order shown (top-to-bottom or numerical) but may be performed in other orders. Additional, different, or fewer acts may be used. For example, an act for applying the machine-learned model 310 is provided without or in addition to the storing in act 520.

The system of FIG. 3 or a different system performs the acts. For example, a computer or server with access to a database storing the training data obtains the data and performs the machine training 510. The resulting trained model is stored 520 in the database and/or a different memory.

In act 500, a processor obtains training data. The training data is obtained from a memory, such as a database, transfer over a computer network, and/or by loading from a removable storage medium. Alternatively, or additionally, the training data is obtained by mining or searching patient records or data stored from prior operations. The training data may be created by expert curation, simulation, experiments, studies, and/or automated extraction.

For machine training, hundreds, thousands, or more samples of input and outputs are obtained. For example, many samples of surgical images with designated or labeled lengths during surgery are acquired. Multiple ground truth lengths may be provided for each sample, such as lengths for different points in time during pulling or running the bowel. In one embodiment, the surgical images are video streams from endoscopes in gastric bypass surgeries. The lengths are of biliary or alimentary loops being pulled or run for measurement. As another example, many samples of surgical images with designated or labeled locations of incision during surgier are acquired.

The ground truth lengths or location may be acquired based on expert curation or measured lengths in past surgeries. For example, the lengths as measured with an inserted tape measure are used. As another example, the lengths for the training data were measured with an optical sensor and laser projector. An optical sensor is used for accurate distance measurement in surgeries to create the training data. The distance measurement is based on the triangulation principle. A laser beam strikes the anatomy as a small point or pattern. The receiver of the sensor (photodiode line) detects the position of this point or pattern. The angle of incidence changes according to the distance, and thereby the position of the laser point on the receiver. Other sensors may be used to measure length for the training data. For example, electromagnetic or other position sensing is used to measure distances, such as based on movement of the instruments 1159 being used to run a bowel.

Other information may be obtained, such as additional inputs. For example, pre-operative images and/or clinical data are provided for some or all the samples. The surgical images are endoscope (camera or optical), but different modalities may be used for all or for some of the surgical images.

The training data may be samples for a particular surgical system. For example, the training data is for a manually operated catheter and/or endoscope system. As another example, the training data is obtained for a surgical robotic system. The samples are from previous uses of the type of surgical robotic system. Alternatively, the samples are from various surgical systems.

The surgical images may be pre-processed. For example, registration is used to align the images. Normalization may be used to normalize the intensities of the images. Scaling or other transformation may be used to alter one or more images to a same standard.

The machine learning model has defined inputs and outputs. Each of the training samples obtained include sets of the inputs and corresponding output.

In act 510, the processor machine trains the machine learning model. The processor trains the model to generate the output location or length in response to input of the information (e.g., surgical images). Using the many samples in the training data, the machine training optimizes the values of the learnable parameters of the defined model architecture to generate the output length or location. For example, the model is trained to output length being pulled for measurement.

The training creates models for specific circumstances. For example, the model is trained with samples from surgical robotic systems to create a model for surgical robotic systems. Alternatively, the model is trained for any surgical system for a given type of surgery (e.g., RYGB).

In act 520, the processor stores the machine-learned model in a memory. The architecture and the values of the learned (learnable) parameters are stored. The model as learned is stored for application by the same processor or a different processor. The machine learning model as trained is stored for use with a patient (i.e., with unseen inputs) to generate a measurement (e.g., location for a given length).

FIG. 6 shows one embodiment of a method for measurement for a surgical system. A machine-learned model 310, as trained, is used to output information (e.g., length pulled). A length pulled corresponds to a length to a current location. In alternative embodiments, the machine-learned model 310 outputs a location, such as a location at a given length from a starting point. Based on guidelines and/or pre-operative planning for a given patient, a length along the bowel or other anatomy is used to locate an optimum incision position. The machine-learned model 310 provides efficient and accurate length or location measurement during surgery.

The method of FIG. 6 is performed by the surgical system of FIG. 1, 2, or 3 or another surgical system. In one embodiment, the surgical system of FIG. 3 performs the method. An endoscope or another medical imager captures surgical images of the patient during the surgery in act 600. A programmed image processor 340 (also referred to here as processing logic or circuit) measures the anatomy based on the surgical image. The artificial intelligence is used in act 610 to measure the anatomy. A display screen displays the measurement in act 620. A non-transitory memory 300 may store instructions for the programmed processor 340 to measure and/or the machine-learned model or models 310.

The acts are performed in the order shown or a different order. Additional, different, or fewer acts may be provided. For example, acts for connecting the surgical instrument 1159 to the robotic arm 1139 and using the surgical robot are provided.

In act 600, a camera (e.g., endoscope 1013) captures a video stream. One or more images are captured in other embodiments. The images are captured during surgery, such as while one or more instruments 1159 are within the patient or a surgical opening has been created in the patient.

The images are captured with an endoscope. For a video, the sequence of images or video is captured as the endoscope and/or anatomy is moved, such as by a surgical robotic system or manually by a physician. Another medical imager or a combination of medical imagers (e.g., endoscope and computed tomography) may be used.

In act 610, an image processor measures a length along a biliary loop, an alimentary loop, or another anatomy. The measurement is by a machine-learned model in response to input of the video stream or image. The image processor inputs the surgical images to the machine-learned model, which then outputs the length in the form of distance or location. In response to input of the surgical images for a given patient during surgery, the machine-learned model outputs the length. More than one length may be output, such as outputting lengths at different times during running of the bowel. As more images are input, the length is changed to reflect additional bowel being pulled or run.

In one embodiment, the length along the biliary loop or alimentary loop at which a surgical instrument is located is output by the machine-learned model. In another embodiment, the length is output as a position along the biliary loop or alimentary loop for operating on the biliary loop or alimentary loop. As another embodiment, the length is output as a position at a given distance from a starting point, such as a location at 40 cm of the 60 cm to be pulled.

In act 620, a display displays the length or corresponding location. The location based on the length or the length of the anatomy during the surgery (e.g., gastric bypass surgery) is displayed. The length may be displayed as a measurement of a current distance along the anatomy (e.g., along the biliary or alimentary loop). The length may be a total length to reach the location for operating on tissue. The length along the anatomy gives the location.

In one embodiment, the endoscope captures a video as the anatomy is run or pulled, such as repetitively walking or stepping along the bowel. The entire video is then input to the machine-model, which outputs the total length or location with or without lengths and locations for each step. In another embodiment, an image or sequence of images for each grasping or pulling (i.e., each step of walking through the bowel) of the anatomy is input to the machine-learned model, which outputs the length or location. As represented by the arrow from act 610 to act 600, this is repeated and the lengths or locations from each repetition or step in running the anatomy are added to provide a total length or final location. The display in act 620 may display the total length or final location and/or the lengths or locations for each repetition or step.

In other embodiments, a method is provided for intra-operatively determining incision locations or length in a small intestine during or for a gastric bypass procedure. A machine learning model is trained from a training set including a set of CT images for respective patients, and patient data describing characteristics of a patient associated with the CT images. The CT images are labeled with the length or locations. The model is trained with this training data. For application, patient data is obtained for a target patient. Clinical data (e.g., height and gender) and a pre-operative CT image of a target small intestine of the target patient are obtained. A desired limb length is determined based on the patient data. The desired length or location of incision along the intestine is determined by a surgeon, machine-learned model, or a look-up table based on height, gender, or other clinical data. For example, the pre-operative CT image is applied to the machine-learned model to predict the incision location for bypass. The length and/or location are output for pre-operative planning. The incision location is where to cut and/or where to reattach.

This pre-operative location or length is then used in the surgery. During surgery, a live image of the target small intestine is captured intra-operatively, such as an endoscope capturing an image within the abdominal cavity. The pre-operative CT image is registered to the live image to map the predicted incision location in the CT image to a predicted incision location in the live image. The predicted incision location is overlaid on the live image, which is output to a display screen.

Intra-operative images may be used to train the model to predict the incision location or length pulled based on intra-operative imaging. For application, a live image of the target small intestine is captured intra-operatively. The machine-learned model is applied to the live image and outputs the incision location and/or length.

In some embodiments, the length and/or incision location are used to guide a surgical tool. The surgical tool is positioned a given length along the small intestine and at the incision location. The predicted location and/or length is used to guide the surgical tool to the incision location. For example, a robotic arm is guided by a controller and/or surgeon to position the surgical instrument at the incision location.

The above description of illustrated embodiments of the invention, including what is described below in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize. These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A method for loop measurement for a surgical system, the method comprising:

capturing a video stream from an endoscope held by a first robotic arm of a surgical robotic system, the video captured intra-operatively during minimally invasive surgery where the surgical robotic system pulls a biliary loop or an alimentary loop with a surgical tool connected to a second robotic arm;

measuring, by a machine-learned model in response to input of the video stream, a length along the biliary loop or the alimentary loop from a start location to a grasp point of the surgical tool held by the second robotic arm, the machine-learned model configured to output the length in response to the input of the video stream to the machine-learned model;

displaying the length or a location based on the length during the minimally invasive surgery.

2. The method of claim 1 wherein measuring comprises outputting the length along the biliary loop or alimentary loop at which a surgical instrument is located, the length output by the machine-learned model.

3. The method of claim 1 wherein measuring comprises outputting the length as a position along the biliary loop or alimentary loop for operating on the biliary loop or alimentary loop.

4. The method of claim 1 wherein capturing comprises capturing by the endoscope as the endoscope is moved by a surgical robotic system.

5. The method of claim 1 wherein capturing comprises capturing by the endoscope as the endoscope is moved manually by a physician.

6. The method of claim 1 wherein displaying comprises displaying the length as a measurement of a distance along the biliary loop or the alimentary loop from the start location to the grasp point.

7. The method of claim 1 wherein displaying comprises displaying the location for operating on tissue, the location determined from the length along the biliary loop or the alimentary loop.

8. A surgical system for measurement during surgery, the surgical system comprising:
- a medical imager configured to capture an image of anatomy during surgery for the anatomy;
- an image processor configured to determine, by a machine-learned model in response to input of the image, a distance along the anatomy from a start location to a surgical tool grasp location, the machine-learned model configured by training where the training data includes ground truth measurements from an inserted tape measure and/or an optical sensor, the machine-learned model configured to output the distance; and
- a display configured to display a location of the anatomy during the surgery based on the distance determined by the machine-learned model.

9. The surgical system of claim 8 wherein the medical imager comprises an endoscope, further comprising a first robotic arm configured to move the endoscope within a patient where the image is from within the patient.

10. The surgical system of claim 9 further comprising a second robotic arm configured to pull the anatomy with the endoscope positioned outside the anatomy, wherein the distance comprises an amount of the anatomy pulled by the second robotic arm.

11. The surgical system of claim 8 wherein the surgery comprises gastric bypass surgery, and wherein the distance comprises a distance along a biliary or alimentary loop.

12. The surgical system of claim 8 wherein the location comprises a location of a surgical tool with the distance being along the anatomy to the surgical tool as the surgical tool grasps the anatomy.

13. The surgical system of claim 8 wherein the location comprises the location for surgery on the anatomy.

14. The surgical system of claim 8 wherein the display is configured to display the location on the image.

15. The surgical system of claim 8 wherein the display is configured to display the location on a pre-operative image.

* * * * *